United States Patent [19]

Frenkel et al.

[11] 4,327,712
[45] May 4, 1982

[54] IMAGESCOPE

[76] Inventors: Richard E. Frenkel; Barbara I. Frenkel, both of 33 Park Rd., Scarsdale, N.Y. 10583

[21] Appl. No.: 99,883

[22] Filed: Dec. 3, 1979

[51] Int. Cl.³ .............................................. A61B 1/06
[52] U.S. Cl. ..................................... 128/22; 128/1 R
[58] Field of Search ................. 128/9, 10, 11, 12, 13, 128/14, 15, 16, 17, 18, 19, 20, 21, 22, 23, 1 R; 350/315, 55, 288, 351; 35/59; 40/219

[56] References Cited

U.S. PATENT DOCUMENTS 2,085,180  6/1937  Bevis .................................. 434/371
3,326,204  6/1967  Frenkel et al. ...................... 350/315

Primary Examiner—Robert W. Michell
Assistant Examiner—T. Wallen
Attorney, Agent, or Firm—Bruce M. Eisen

[57] ABSTRACT

Apparatus is provided to facilitate viewing of one's facial image under controlled illumination patterns for purpose of either psychotherapy or merchandise selection.

8 Claims, 4 Drawing Figures

IMAGESCOPE

This invention relates to a novel device, hereinafter called an imagescope, which utilizes controlled viewing of one's facial image under selected conditions. In one subgeneric embodiment, the device can assist an individual in treating his emotional disorders. In another subgeneric embodiment, the device can serve as a merchandising aide to assist an individual in choosing or purchasing an item with a greater prospect he will later be satisfied with it.

Conventional psychotherapy generally consists of prearranged periodic conferences between the therapist (e.g. psychiatrist, psychologist) and the patient. Such conferences are expensive, inconvenient and generally do not occcur at the time when the patient is experiencing acute distress, e.g. anxiety, depression. Although a psychiatrist can prescribe various psychopharmaceuticals for the patient, chronic reliance on drugs is undesirable.

A technique for psychiatric observation purposes had previously been disclosed in Frenkel et al, U.S. Pat. No. 3,326,204. Therein, in the course of a session with a therapist, the patient is instructed to view his facial expressions under natural or colored lighting. The patentees teach a rather cumbersome device to facilitate this technique comprising a local light source focused on the patient and color filters situated in one embodiment between the patient and a mirror, and in another embodiment between the light source and the patient viewing the mirror. The therapist varies the color by rotating a roller on which is wound the colored lenses. In still another variant, the colored filter surrounds the main light source for room illumination permitting the patient to view himself in a wall mirror while bathed in such light.

Sound recording means can be included in this apparatus to record the patient's verbal reactions. While skillfull use of this device by a therapist can yield valuable analytic information, its use is limited by practical considerations to the conventional therapist-patient session, and offers no relief for out-of-the office patient distress.

We have since discovered that self-viewing by a patient of his facial image can, under controlled illumination, and following initial sessions with a therapist, be usefully undertaken by a patient alone, e.g at home, to beneficially alter undesirable moods and to facilitate recording of patient's verbal behavior at virtually any time.

We have invented a device which can capture or harness this phenomenon in a simple, portable, inexpensive and relatively unobtrusive format. The device can be called on imagescope and in general terms can be described as comprising:
  (a) a mirror
  (b) a plurality of diversely colored electric light bulbs spatially arranged to enable each to illuminate said mirror and be hidden from direct view of the patient.
  (c) a housing containing said light bulbs and supporting said mirror.
  (d) electrical control means for the patient to select a desired illuminating color.
  (e) a tubular structure mounted on said housing surrounding said mirror and having on the other end means to surround the face of the patient and permit him to view his facial image in said illuminated mirror.

This inventive device can be better understood by reference to the Figures which depict a preferred embodiment thereof.

Figure 1:
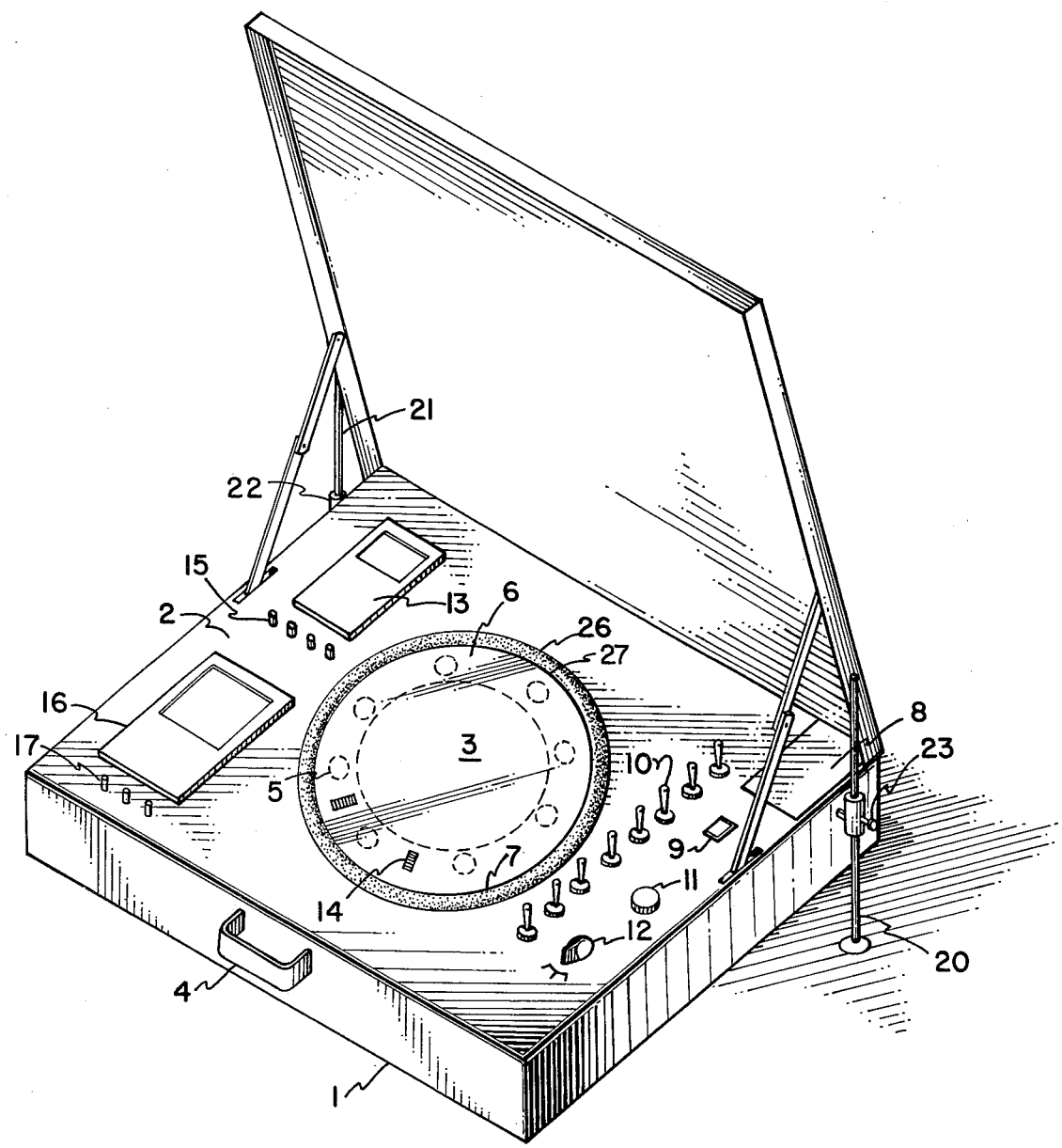
FIG. 1 is a top plan view of the device with the tubular viewer in a collapsed position and the bulb shield removed.

The device housing 2 is seated in a conventional small luggage case 1, equipped with a carrying handle 4. The heart of the imagescope is a mirror 3, surrounded by a plurality of electric bulbs, e.g. 5. An opaque convex shield 6 blocks direct view of the bulbs (In FIG. 1 it is shown as transparent for convenience).

The shield is open on the interior mirror side and has a reflective undersurface. Thus the light from the bulbs is reflected onto the mirror surface. A plurality of small air ports (not shown) are provided under the shield and throughout the housing to vent and dissipate heat buildup from the glowing bulbs. A tubular structure 7 surrounds the perimeter of the shield 6. In FIG. 1 the tubular structure is collapsed for illustrative purposes, while in FIG. 2 it is extended.

The master electric power source 8 is a conventional lead (wires not shown) to household current and/or a conventional battery pack. Switch 9 acts as a master switch for the electric power. The bulbs are individually wired in simple manner to the electric power source 8, each passing through and utilizing a separate switch (e.g. 10). When the switch is in the "on" position, the circuit is closed and the respective bulb lights. Two or more switches can simultaneously be "on" to blend their resultant colors. Beside each switch in the 10 series is written the color bulb it controls and/or the switch can be color-coded.

In a preferred embodiment the circuit from the master switch passes through a rheostat 11 and an electromechanical circuit interrupter 12 before leading into the color control switch 10. The rheostat, of standard construction and operation, permits the patient to control the intensity of the light bulbs. Similarly, the electromechanical circuit breaker, of standard construction and operation, permits the patient to produce a controlled flickering of the light bulbs. These features permit the therapist and patient a greater array of illuminating patterns to choose from in experimenting with and positively altering the emotional state of the patient.

In the preferred embodiment, the imagescope also contains a tape recorder 13, also powered by electric source 8 through conventional wiring (not shown) and activated by controls 15 (on/off switch, volume control dial). Closing the circuit by turning switch 15 on, also activates microphone 14, supported on shield 6. Thus the patient speaking into tube 7 will activate the microphone, causing tape recorder 13 to record the patient's comments. This feature is highly desirable in combination with a tape player 16. Controls 17 therefore include the standard on/off, volume, fast, forward and rewind controls, common on tape players. Through simple wiring, the master electric power source also powers the tape player.

Figure 2:
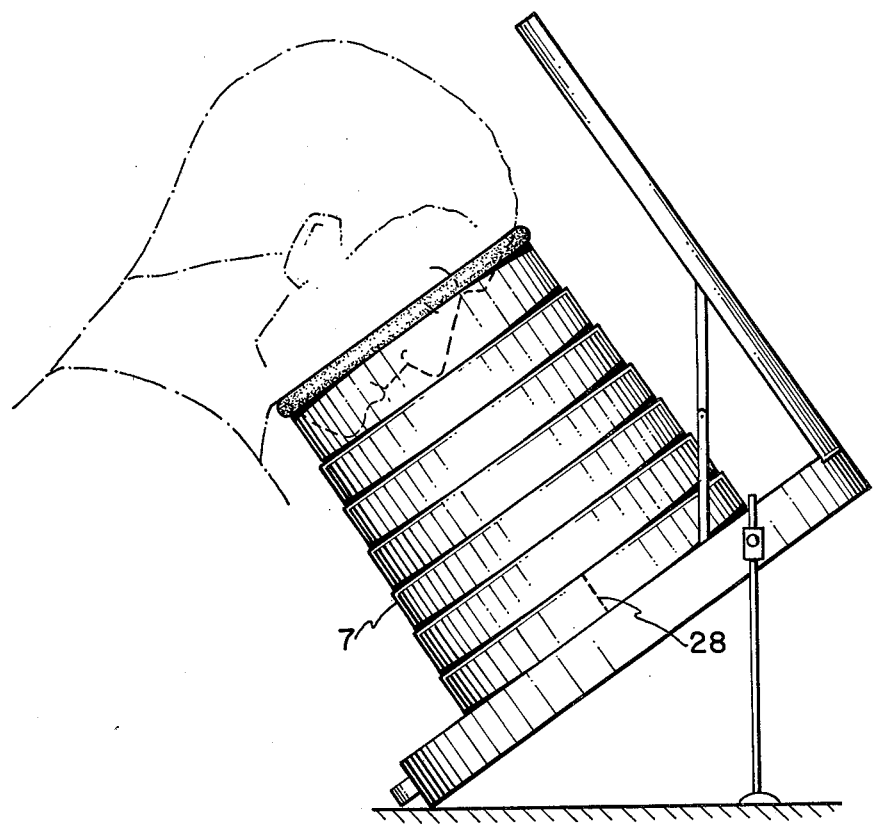
FIG. 2 is a side elevational view of the device as utilized by a patient.

The tubular structure shown in FIG. 2 is of the collapsible type comprised of telescoping cylinders of slightly increasing diameter held upright by friction fit similar to the commonplace collapsible metal cups. The rim at the viewing end of the tube is preferably lined with a soft foam material to cushion the patient's face. In a highly preferred embodiment, the tube 6 is provided with a removable septum for purposes described below. The tube end is crimped around a collar surrounding the shield which has an inwardly folded edge. This crimping retains the tube on the collar while permitting free rotation therearound.

The case 1 can be set and maintained at the elevation and angle most comfortable for viewing by means of metal rods 20 and 21. They can be stored, for example, in the front part of the case by clips (not shown). During use they are inserted in brackets 22 and 23 (not visible) and held in place by tightening the screw.

Numerous mechanical and electric variants of the foregoing are of course possible and within the scope of this invention. The housing 3 not need be seated in a case. The tube 7 need not be collapsible nor permanently affixed to the housing. For example, a rigid tubular member can be a separate element temporarily held onto the housing by tongue-in-groove mating arrangements with corresponding grooves or slats. Similarly the patient's concurrently recorded comments can help the therapist facilitate total treatment. In other words, "seeing oneself" in the imagescope bathed in a characteristic background color/illumination pattern(s) can trigger memory-associated positive feelings to overcome or inhibit negative feelings. These charcteristic color/illumination pattern(s) are specific to the patient's unique life experience and can most effectively be identified in conjunction with a trained therapist, particularly taking advantage of the tape playing and tape recording features described above.

The imagescope of this invention can be utilized as follows:

In the course of guided discussion between the trained therapist and the patient, the patient will be asked to view his image in the scope while the therapist operates the device to cause selected illuminating colors. Viewing the image through the tube avoids peripheral distractions and greatly enhances the effective concentration of the patient. The result of the circumscribed field is a powerful magnification of the intensity of the psychovisual stimulation.

The electrical circuitry can be designed to optionally permit remote control by the therapist similar to remote control of a television set. This is particularly useful during diagnostic use of this device by the therapist. Similarly, the housing can be provided with a live microphone for the therapist's voice.

Figure 3:
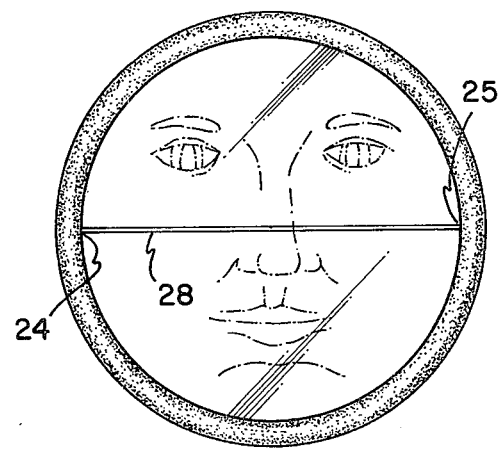
FIG. 3 is a view of what the patient in FIG. 2 sees.

In a highly preferred embodiment of this invention the tubular viewing means is provided with a septum as shown in FIG. 3. This enables the patient to view half of his facial image in a different color from that of the other part of the face. We have surprisingly found that such a split image can elicit valuable responses, including those leading to significant diagnostic information. The tube 7 can be rotatable with the septum 28 fixed therein, held in part in opposite interior tracks or grooves 24 and 25 in the lower part of the tube. In utilizing a two-part tube the septum (formed from an opaque plastic sheet, for example) sits in the lower part. The tube bottom itself sits in the groove between two concentric rings 26 and 27. Thus the tube is loosely held in place permitting free rotation thereof. Two protuberances at opposite points on the outside of the lower tube member can facilitate rotation by the patient.

In another embodiment, this device can be used to test for drugs useful in the treatment of mental illness. This is based on the theory that agents which affect color perception may have a profound effect on the brain. In accordance with this method the patient is first tested for color reaction without use of any drugs. Then a test drug is administered to see if it effects color perception.

In still another embodiment, the mirror is transparent on the opposite side, that is the therapist can view or record (by a suitable instrument) the patient's pupillary response to the various color patterns. Such data, as comparative pupil diameter, can provide diagnostic and comparative information.

Although we do not wish to be bound or limited by our theory behind this phenomenon (that viewing of one's facial image under controlled conditions can improve the emotional state) we offer the following hypothesis at least as partial explanation:

While cognitive information is being received and stored by the brain, it generally takes place against a visual backdrop. Although the person is rarely cognizant at the time of this visual field, it too is associatively stored by the same neurochemical mechanisms responsible for memory and emotional storage.

Often the most emotionally significant message inputs are of a repetitious nature and take place against a constant visual backdrop characterized by a distinctive color and design pattern. For example, a child over the course of years experiences repeated parental rejection particularly during mealtimes in a kitchen having a distinct green-colored decor. Among his happiest moments are periodic, prolonged visits at his aunt's house where warm attention is showered upon him, often during mealtime in the aunt's bright yellow kitchen. The feeling of parental rejection is based in reality and can never be erased or undone. For this individual who later in life seeks a therapist's help for recurrent depression, viewing his facial image in the imagescope bathed in bright yellow light may improve his mood by surfacing the associatively-stored warm and ego-strengthening memories and feelings. Certain changes in light intensity and constancy (flickering) may further heighten this effect. One explanation is that the rods of the eye are the input source for factual information and transmit in black and white while the cones are responsible for emotional input and transmit in color.

As part of an overall therapeutic program, the psychiatrist's recorded comments and questions can catalyze and direct this process.

Figure 4:
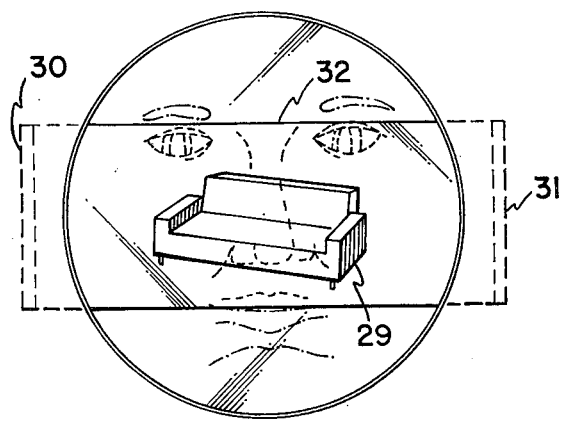
FIG. 4 is a view of the invention used as a merchandizing device.

When utilized as a merchandizing device, a clear film is passed through the tube at the bottom just above the shield level. On the transparency (32) are outlines (29) of the style of the object sought to be purchased, i.e. furniture, clothing, automobiles. The prospective purchaser can first view a plurality of styles in white light. When a style of interest is identified, the viewer then utilizes the color controls to determine the color-style combination that is most satisfying psychologically. The film is mounted in simple fashion on rollers (30,31) which can be manually or electrically advanced. FIG. 4 illustrates a sample view.

Numerous other variants of the imagescope of this mention will be apparent to one skilled in the art.

We claim:

1. A psychotherapeutic imagescope useful in the treatment of a patient suffering emotional disorders comprising
   (a) a mirror;
   (b) lighting means capable of directly illuminating said mirror with a plurality of diverse colors and hidden from direct view of the patient;
   (c) a housing containing said lighting means and supporting said mirror;
   (d) electrical control means on said housing for the patient to select a desired illuminating color;
   (e) a tubular structure mounted on said housing surrounding said mirror and having on the other end means to surround the face of the patient and permit him to directly view his facial image in said illuminated mirror.

2. An imagescope according to claim 1 which additionally contains electrical control means to vary the intensity of the light.

3. An imagescope according to claim 1 which additionally contains means to periodically interrupt the light.

4. An imagescope according to claim 1 which is seated in a portable carrying case.

5. An imagescope according to claim 1 wherein said mirror is transparent from the side opposite the patient's viewing side.

6. An imagescope according to claim 1 which additionally contains means to tape record the patient's voice.

7. An imagescope according to claim 1 which additionally contains means to play a prerecorded tape.

8. An imagescope according to claim 1 which additionally contains a septum in the portion of said tubular structure adjacent the mirror, thereby bifurcating the facial image.

* * * * *